(12) United States Patent  
Gaston et al.

(10) Patent No.: US 10,376,389 B2  
(45) Date of Patent: Aug. 13, 2019

(54) MYOELECTRIC PROSTHESIS AND METHOD

(71) Applicants: Glenn Gaston, Charlotte, NC (US); Bryan Loeffler, Charlotte, NC (US)

(72) Inventors: Glenn Gaston, Charlotte, NC (US); Bryan Loeffler, Charlotte, NC (US)

(*) Notice: Subject to any disclaimer, the term of this patent is extended or adjusted under 35 U.S.C. 154(b) by 38 days.

(21) Appl. No.: 15/610,778

(22) Filed: Jun. 1, 2017

(65) Prior Publication Data

US 2018/0116829 A1    May 3, 2018

Related U.S. Application Data

(60) Provisional application No. 62/415,872, filed on Nov. 1, 2016.

(51) Int. Cl.
| | |
|---|---|
| *A61B 5/00* | (2006.01) |
| *A61F 2/58* | (2006.01) |
| *A61F 2/72* | (2006.01) |
| *A61B 5/0488* | (2006.01) |
| *A61B 5/0492* | (2006.01) |
| *A61F 2/76* | (2006.01) |

(52) U.S. Cl.
CPC ............ *A61F 2/72* (2013.01); *A61B 5/04888* (2013.01); *A61B 5/6806* (2013.01); *A61B 5/6825* (2013.01); *A61F 2/583* (2013.01); *A61B 5/0492* (2013.01); *A61B 5/6826* (2013.01); *A61F 2002/7615* (2013.01)

(58) Field of Classification Search
CPC .... A61F 2/583; A61F 2/72; A61F 2/06; A61F 2/08; A61F 2002/0894; A61B 5/04888; A61B 5/6825
See application file for complete search history.

(56) References Cited

U.S. PATENT DOCUMENTS

| | | | |
|---|---|---|---|
| 2013/0253705 A1* | 9/2013 | Goldfarb | A61F 2/583 700/260 |
| 2014/0058524 A1* | 2/2014 | Gray | A61F 2/2846 623/20.17 |

OTHER PUBLICATIONS

Boffeli, Troy. Complete Fifth Ray Amputation with Peroneal Tendon Transfer—A Staged Surgical Protocol. The Journal of Foot and Ankle Surgery. 51 (2012) 696-701.*
Dumanian, Gregory. Targeted Reinnervation for Transhumeral Amputees: Current Surgical Technique and Update on Results. Plastic and Reconstructive Surgery: Sep. 2009. vol. 124, Issue 3. 863-869.*
Cheesborough, Jennifer. Targeted muscle reinnervation in the initial managemetn of traumatic upper extremity amputation surgery. American Association for Hand Surgery. Jan. 16, 2014. 9:253-257.*
Saremi Hossein. Tendon Transfer in Hand Trauma: A Case Report. Trauma Monthly. 2013:17)4). 401-403.*
Stevanovic, Milan. Functional free muscle transfer for upper limb reconstruction. Plastic and reconstructive surgery. Aug. 2014. Issue 2, 157-274.*

(Continued)

*Primary Examiner* — Christie L Bahena
(74) *Attorney, Agent, or Firm* — Fox Rothschild LLP

(57) ABSTRACT

A method of transferring intrinsic hand muscles along with a respective nerve and blood supply; and allowing signal detection by a surface electrode is provided. The method further includes transferring muscles of a forearm along with a respective nerve and blood supply; and allowing signal detection by a surface electrode.

3 Claims, 15 Drawing Sheets

(56) References Cited

OTHER PUBLICATIONS

Treatments. Hospital for Special Surgery. Verified by the Wayback machine Oct. 2014.*
Common Problems, Conditions, & Treatments. Premier Orthopaedic and Hand Center. 2011.*
Dodson, Robert. Case study: Surgical, prosthetic and therapeutic considerations for a patient with ipsilateral brachial plexus injury and transradial amputation. MEC 2011 Prosthetics Symposium. Aug. 14-19, 2011.*
Monreal, Ricardo. Restoration of finger flexion by pronator teres muscle transfer after brachial plexus injury: A case report. Hand. Sep. 2013; 8(3): 334-338.*
Gaston, M.D., et al.; "A Novel Muscle Transfer for Independent Digital Control of a Myoelectric Prosthesis: The Starfish Procedure;" J. Hand Surg. Am., ASSH, Elsevier, Inc., Jun. 2018; pp. 1.e1-1.e5. USA.

* cited by examiner

MYOELECTRIC PROSTHESIS AND METHOD

CROSS REFERENCE TO RELATED APPLICATIONS

This application claims the benefit of U.S. provisional application Ser. No. 62/415,872, filed on Nov. 1, 2016; the entirety of which is incorporated by reference herein.

FIELD OF THE INVENTION

This invention relates to medical devices with surface electrodes for detecting signals produced by muscles thus allowing prosthetic control (referred to from this point forward in this application as myoelectric prosthesis). Specifically, this application refers to a method of muscle and nerve transfers to allow new signals to be detected by surface electrodes and allow additional myoelectric inputs for myoelectric prostheses.

BACKGROUND OF THE INVENTION

There are several types of prostheses available for upper extremity amputees including passive devices, body powered devices and myoelectric devices. Passive devices are primarily for cosmetic appearance with limited functional benefit. Body powered devices require the use of the shoulder and/or elbow to open and close a terminal device. There are many types of terminal devices that can be used and the use of these prostheses is widespread and favored in many specific circumstances. Myoelectric prostheses rely on the detection of a signal produced by muscle contraction in the residual limb to power the terminal device. These have several advantages compared with passive devices and body powered devices including lower energy requirements for use and proportional control. The advent of myoelectric prostheses has revolutionized the field of upper extremity prosthetics, but there are many persisting limitations.

The field of prosthetics has seen many recent advancements thus improving the quality of life for amputees. Despite this, these advanced prosthetics are limited by the human-prosthesis interface. For myoelectric prostheses, the mode of interaction for signaling the prosthesis has been via surface electromyography (EMG). For bidirectional control in a single plane, two EMG channels are needed. Because of the limited number of muscles available to serve as independent signals for the fingers, individual digital control with myoelectric prostheses has not been possible for patients with partial or total hand amputations. Having an appropriate number of muscles available, ideally with the same desired function, is a requisite for successful myoelectric prosthetic use. The lack of available muscle signals has limited the functional ability for patients with partial hand amputations, total hand amputations, below elbow amputations, above elbow amputation, and shoulder disarticulations.

Currently there are limited control options for individuals that have undergone a partial hand amputation. The mechanical fingers of a myoelectric hand are capable of independent finger flexion and extension only if the requisite muscle signals are available. The first myoelectric prosthesis was designed by Reiter in 1948 and provided finger flexion and extension by use of a single muscle. Clinically this is not preferred since independent and intuitive control is not provided due to the lack of available EMG signals from appropriate muscle groups. The level of amputation determines available muscles for surface EMGs and in turn the ability to control multiple degrees of freedoms. A typical partial hand myoelectric fitting consists of two or three surface electrodes that capture EMG readings from either intrinsic hand muscles or from more proximal wrist and finger flexor and extensor muscle groups allowing control of hand opening and closure. While forearm musculature produces reliable signals, prosthetic control is not natural as the muscle contraction is not associated with the desired prosthetic finger motion.

For below elbow amputations at the level of the forearm, amputees have been limited in achieving all of the normal degrees of freedom possible for the wrist, forearm and hand function due to the limited EMG inputs available to control the desired degrees of freedom. Basic options such as grasp and release are possible, but control of functions such as radial deviation, ulnar deviation, wrist flexion, wrist extension, pronation and supination have not been possible due the limited number of EMG signals available. Independent control of the thumb and fingers has also not been possible due to inadequate signals available for detection.

In above elbow amputees including shoulder level disarticulations, targeted muscle reinnervation (TMR) has allowed an increase in the number of signals available. Nerves that previously controlled the forearm and hand, which are still present in the residual limb, can be transferred into a remaining muscle in the upper arm or shoulder to produce a new and unique signal for detection. For above elbow amputees transfers such as the median nerve into one head of the biceps, for example, allows one head of the biceps to control elbow flexion and the re-innervated head of the biceps to control grasp of the hand. Similarly, TMR can be performed using the radial nerve to re-innervate one head of the triceps to allow digital extension in addition to the previously possible elbow extension.

An advanced recent prosthetic design and technology known as pattern recognition allows a greater number of muscles to be detected for specific patterns of prosthetic use. This technique involves placing multiple surface electrodes on the skin and using a computer to analyze the pattern of muscle contracture for a given function. This pattern can then be used to direct myoelectric prosthetic control rather than relying on a direct individual muscle contracture for the function. This has been more widespread in above elbow amputees but is possible for below elbow amputees as well. The limitation of this technique is the inability to preform multiple planes of motion simultaneously and independently. The advantages of one muscle controlling one function includes the highly intuitive nature of prosthetic control, the ability to detect multiple EMG inputs that are each specifically linked to a particular function, and to allow these multiple functions to occur simultaneously in a coordinated and intuitive manner.

An additional limitation in optimal control of a myoelectric prosthetic is cross-talk. Cross-talk occurs when multiple muscles are producing multiple signals simultaneously thus making detection of one specific signal difficult. This unwanted detection of signals from muscles other than the target should be minimized when possible with surgery. The previously described method of limiting cross-talk involves the use of adipofascial flaps that are placed between adjacent muscles.

The largest current limitation of myoelectric prostheses for upper extremity amputees centers on the need for a greater number of available myoelectric signals. Through the use of novel muscle transfers and nerve transfers, a much greater number of signals can be detected allowing a new generation of prostheses to be produced thus allowing a higher level of function for these patients.

BRIEF SUMMARY OF THE INVENTION

Myoelectric prostheses, in accordance with the invention of novel muscle and nerve transfers, can address the deficiencies of current prosthetics namely the inability to simultaneously and intuitively control multiple degrees of freedom for the limb.

In one aspect of the invention, a method of transferring intrinsic hand muscles along with a respective nerve and blood supply; and allowing signal detection by a surface electrode is provided.

In another aspect of the invention the method includes transferring muscles of a forearm along with a respective nerve and blood supply; and allowing signal detection by a surface electrode.

In another aspect of the invention the method includes transferring a median nerve in the forearm muscle to a recipient forearm muscle; and producing a signal for detection by a surface electrode.

In another aspect of the invention the median nerve is an ulnar nerve.

In another aspect of the invention transferring a nerve to supinator is to a superficial forearm muscle, such as brachioradialis to control supination of a myoelectric wrist rotator.

In another aspect of the invention transferring a nerve comprises transferring a terminal branch of an anterior interosseous nerve to a forearm muscle or transfer of the pronator quadratus with a neurovascular pedicle for pronation control of a myoelectric wrist rotator.

In another aspect of the invention, interossei muscles can be transferred to the dorsal aspect of the hand to allow independent digital control for partial hand amputees. The first dorsal or volar interosseous muscle can be transferred along with its neurovascular pedicle to allow index finger control. The second or third dorsal interosseous can be transferred to the dorsal aspect of the hand along with its neurovascular pedicle to allow control of the long finger. The second volar or fourth dorsal interosseous muscle can be transferred to the dorsal aspect of the hand along with its neurovascular pedicle to allow control of the ring finger. The third volar interosseous muscle or the hypothenar muscles can be transferred to the dorsal aspect of the hand or proximally into the forearm along with its neurovascular pedicle to allow control of the small finger. The thenar muscles can be transferred either to the dorsal aspect of the hand or proximally in the distal or radial forearm along with its neurovascular pedicle to allow control of the thumb. The lumbrical muscles can be transferred for the four fingers respectively as an alternative donor muscle. In all instances the overlying dorsal skin is thinned to allow greater signal detection.

In another aspect of the invention the metacarpal heads are resected at least 3 cm to allow adequate room for the prosthetic digits on the remaining hand to match the patient's native anatomy and any existing digits. With future design modifications, this distance could be subject to change.

In another aspect of the invention, the volar plate and flexor sheath of each amputated digit is transferred dorsally to serve as an interpositional autograft material between the transferred muscles and prevent unwanted cross-talk. Alternatively, an allograft interpositional material may be used.

In another aspect of the invention, all of the hand intrinsic muscles including the thenar and hypothenar muscles can be transferred to the dorsal aspect of the remaining hand, wrist or forearm along with their neurovascular pedicles including the radial and ulnar arteries as a unit to allow individual control of the thumb, small finger, or all digits in the setting of a complete hand amputation. We have termed the transfer of all of the hand intrinsics including the neurovascular pedicles the STARFISH procedure.

In another aspect of the invention, the median nerve can be transferred into the nerve to the brachioradialis or any other desired forearm muscle to allow an independent myoelectric signal for thumb opposition or palmar abduction.

In another aspect of the invention, the ulnar nerve can be transferred into the nerve to palmaris longus or another residual forearm muscle to allow intrinsic digital control or adduction of the thumb.

In another aspect of the invention, the deeper muscles of the forearm can be transferred into a more superficial location along with their neurovascular pedicles to allow multiple new signal detection and thus an array of new functional options. This includes the flexor digitorum superficialis or profundus for digital flexion. This can be done as a unit for composite grasp, or separately to allow individual digital flexion. This also includes the flexor pollicis longus transfer for independent thumb flexion. This also includes the flexor carpi radialis or flexor carpi ulnaris for wrist flexion. This also includes the flexor carpi ulnaris or extensor carpi ulnaris for ulnar deviation. This also includes the extensor carpi radialis longus or brevis for wrist extension. This also includes the pronator teres or pronator quadratus for pronation. This also includes the extensor digitorum communis, extensor indicis proprius, and extensor digiti quinti for finger extension. This also includes the extensor pollicis longus for thumb extension. Adipofascial flaps or allograft should be used as an interpositional material to limit cross-talk between the individual muscles.

In another aspect of the invention, any of the muscles listed in the above paragraph from the forearm can be transferred above the elbow to allow a greater number of signals available for detection and greater functional capabilities for above elbow amputees.

DETAILED DESCRIPTION OF THE INVENTION

Figure 1:
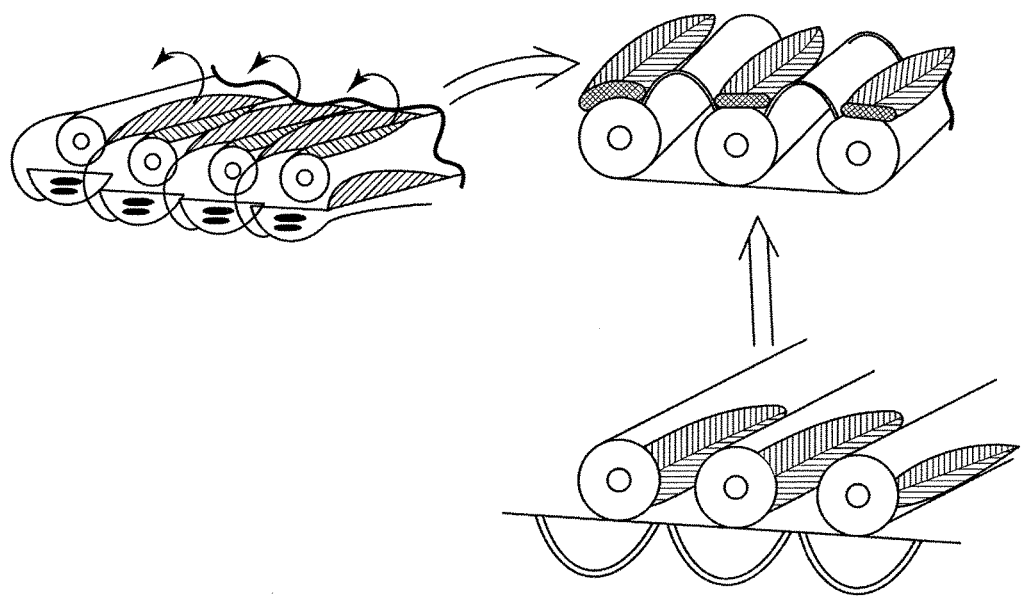
FIG. 1 is an illustration that on the left side and bottom right demonstrate the normal relationship of the interossei muscles between the metacarpal bones with the flexor sheaths palmar. In the top right image the transfer of the interossei with their neurovascular pedicles to the dorsal aspect of the metacarpals along with the interposition of the flexor sheaths is illustrated.
Figure 2:
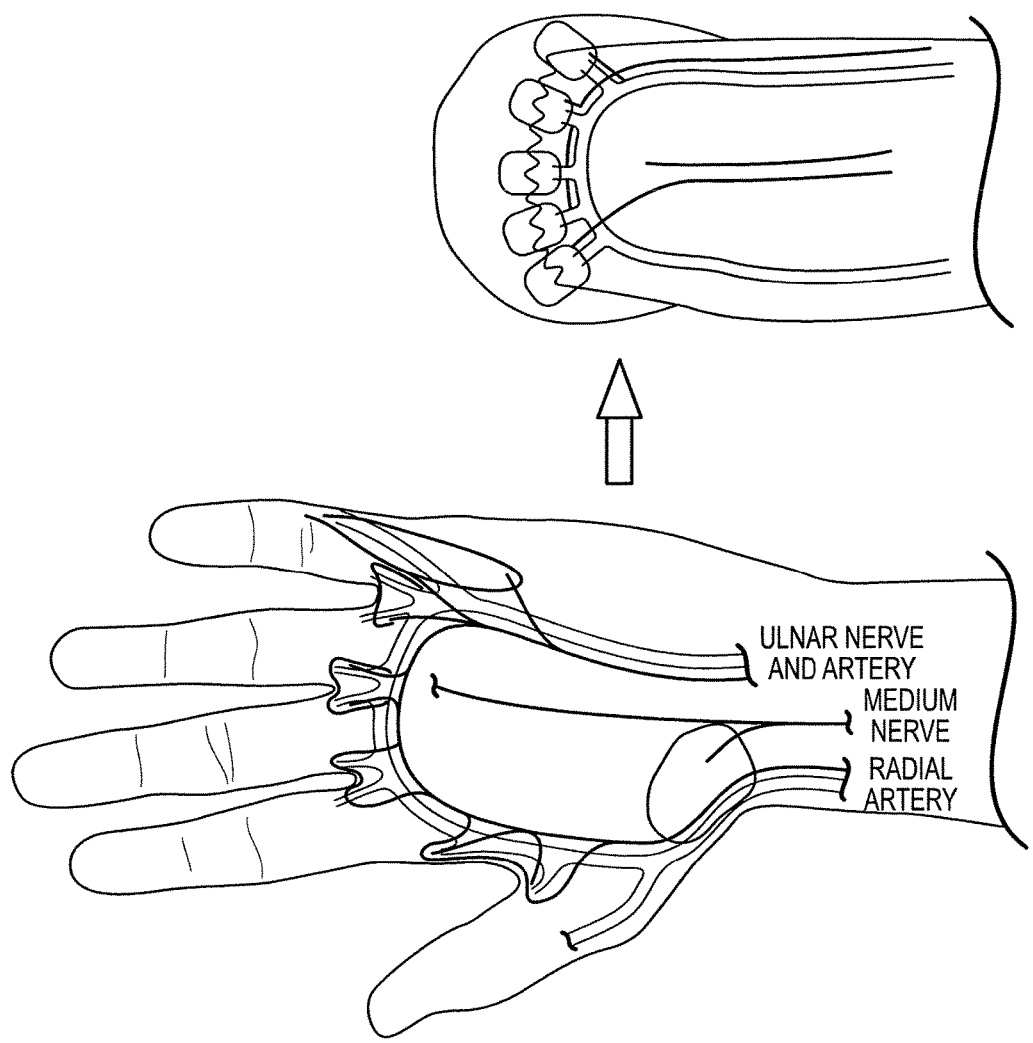
FIG. 2 is depicts the STARFISH procedure. All of the intrinsic muscles of the hand along with their respective innervation from the median and ulnar nerves as well as their vascular supply from the radial and ulnar arteries are mobilized as a unit and transferred into the residual limb (either remaining partial hand, carpus, or distal forearm).

In describing the invention herein, an understanding must be made that this invention is a surgical technique without which a new generation of prosthetics would not be possible. Those prosthetists adept in upper extremity prosthetics will have unparalleled new functional degrees of freedom to offer patients that have undergone surgeries using the techniques described in this invention. While some newer prosthetic designs may be required such as: multichannel microprocessors, multiple motor drivers, multiple EMG inputs, new more powerful or longer lasting power systems, new housing units for the electronic components, new socket designs, and some new componentry to allow these new degrees of freedom, the requisite for all of this is the invention of the surgical technique to provide the necessary signals for detection.

For partial hand amputations, we have demonstrated that the transfer of the interossei muscles to the dorsum of the hand can provide the necessary signals to allow individual finger control. Prior to the advent of this technique, myoelectric prostheses had never achieved this desired function. In the setting of acute partial hand amputations with non-replantable digits, intra-operative nerve monitors can be used to test the interossei and ensure innervation is still present to the desired muscles for transfer. Blood supply can be directly visualized. When the procedure is to be performed in a delayed fashion, standard EMG can be performed to assess the innervation to these muscles and thus their suitability for transfer before surgery. The surgery can then be carried out under general or regional anesthesia. The respective metacarpals are identified for the amputated digits and subperiosteal dissection is carried out to expose the entire metacarpal from the dorsal side. The distal 3 cm including the metacarpal head is then removed. Next the interossei muscles are released from their origin on the metacarpals with care taken to protect their nerve and blood supply. The interossei are then transferred between the metacarpals to reside on the dorsum of the remaining metacarpal shaft. The muscles are myodesed in this position. The flexor sheath is then dissected free and passed dorsal as well to serve as an interpositional material and prevent unwanted cross talk between the transposed interossei muscles. The soft tissues overlying the transposed muscles are then thinned to allow better signal detection without the dampening effects of the subcutaneous fat. Skin grafts or flaps are used as needed for coverage of the residual partial amputation.

After surgery, edema control is initiated and a referral made for prosthetist evaluation. Because of the highly intuitive nature of the muscle control and the amplitude of the muscle contraction, almost immediate signal detection is possible. With this new technique, each previously amputated finger has a new perfectly intuitive signal along the dorsal aspect of its respective metacarpal that allows EMG inputs to be detected that are directly associated with its desired function. With the use of multiple motor drivers, a multichannel microprocessor, and appropriate prosthetic components, independent digital control is possible.

This same approach can be expanded for total hand amputees or patients losing all digits including the thumb with the STARFISH procedure. The radial and ulnar arteries supply the deep and superficial arches which provide the blood supply for all of the intrinsic muscles of the hand (all interossei, thenar, hypothenar and lumbrical muscles). The ulnar nerve motor branch follows the ulnar artery and supplies all of the interossei muscles, the hypothenar muscles, and the adductor pollicis/deep head of the flexor pollicis brevis muscles. The median nerve motor branch supplies the thenar muscles. We have demonstrated in the lab that the radial and ulnar arteries can be raised along with the ulnar and median nerve motor branches with all of the hand intrinsic muscles. This allows all (or the desired) intrinsic muscles to be transferred with blood and nerve supply. Depending on the level of the amputation, these can be transferred to the dorsum of the metacarpals, carpus, or even into the distal forearm. With these additional signals, again along with the prosthetic requirements, individual control of all fingers and the thumb is possible. Clinical scenarios include but are not limited to: trauma, vascular insufficiency, gangrene, tumor resection, congenital defects, and even some forms of severe spasticity or stiffness.

For amputations between the elbow and hand much depends on the exact level of amputation. There are two nerves that previously controlled motor function of the hand that are prone to forming symptomatic painful neuromas: the median and ulnar nerves. These nerves can be used for forearm level targeted muscle reinnervation in the forearm which has not been described. While they can technically be transferred into almost any recipient forearm muscle, we have successfully transferred the median nerve into the nerve to brachioradialis and the ulnar nerve into the nerve to palmaris longus. This not only prevents painful neuroma formation, but allows new signal detection for thumb opposition by the brachioradialis muscle and intrinsic control by the palmaris longus. In the absence of the palmaris longus we would use nerve to flexor carpi radialis.

Figure 3:
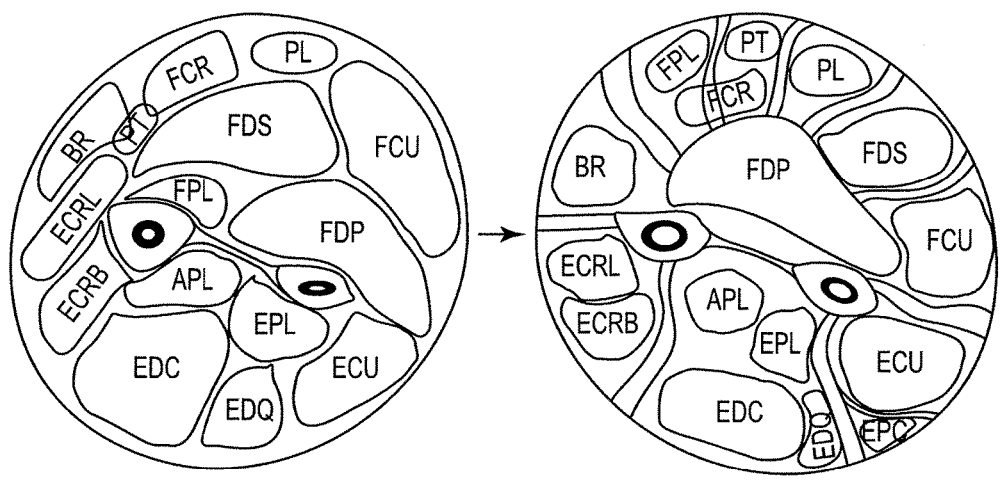
FIG. 3 is an illustration demonstrating the transfer of the proximal or midforearm level musculature along with its neurovascular pedicle to the surface to allow subsequent detectable myoelectric signals. Note the adipofascial flaps or allograft septation used to minimize cross talk. Some muscles such as the EPL may be transferred superficially or left deep depending on the level of the amputation and desired functional gains.
Figure 4:
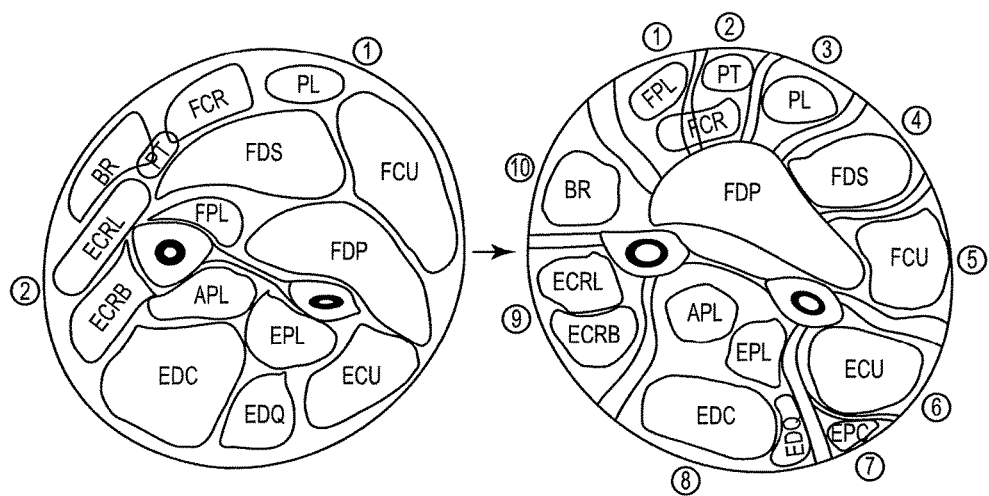
FIG. 4 illustrates the traditional 2 signals used for detection compared with the 10 individually detectable signals after muscle transfer.
Figure 5:
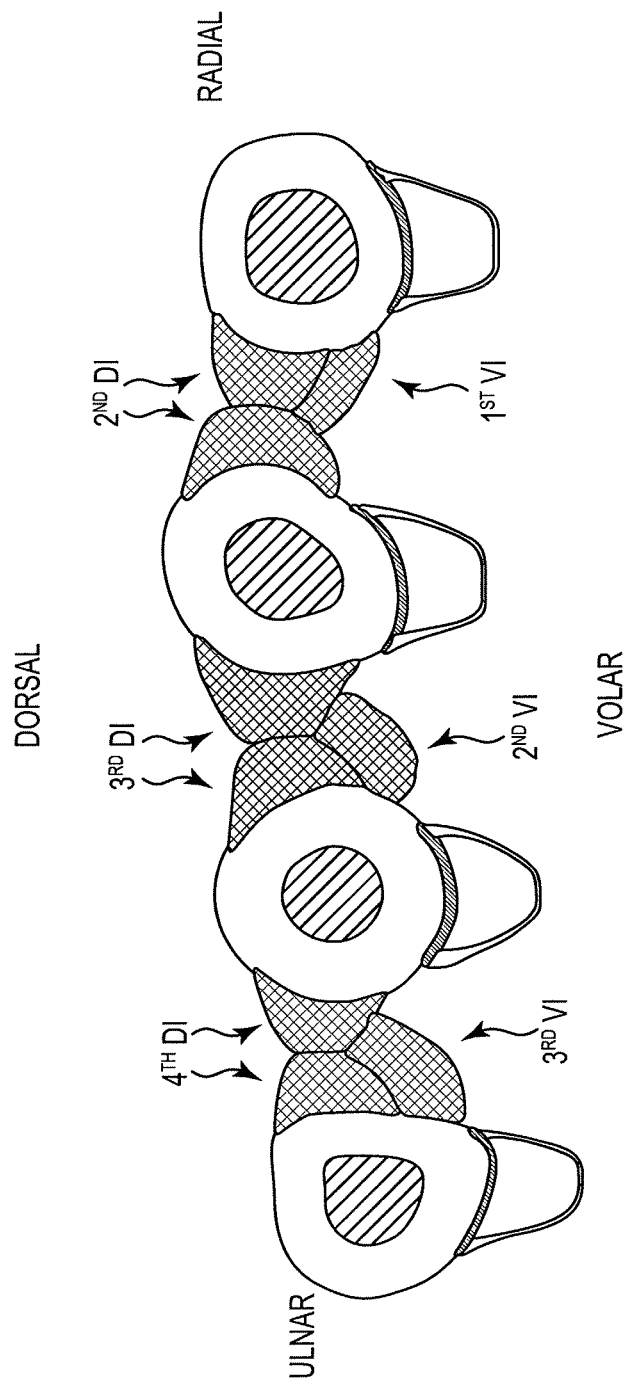
FIG. 5 is a cross sectional view of the transmetacarpal anatomy.
Figure 6:
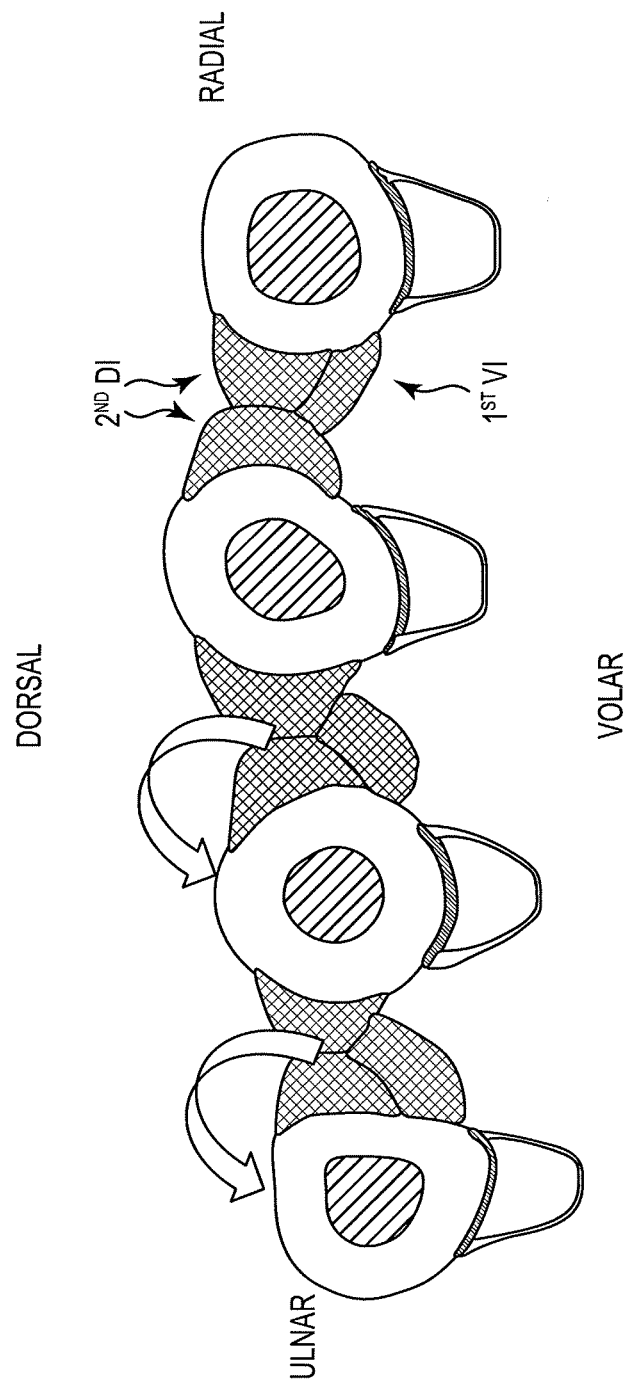
FIGS. 6-15 illustrate the various aspect of the surgical procedure in accordance with the invention. showing the third and fourth interossei muscles being transferred to the dorsal surface of the fourth and fifth metacarpals, respectively.
Figure 7:
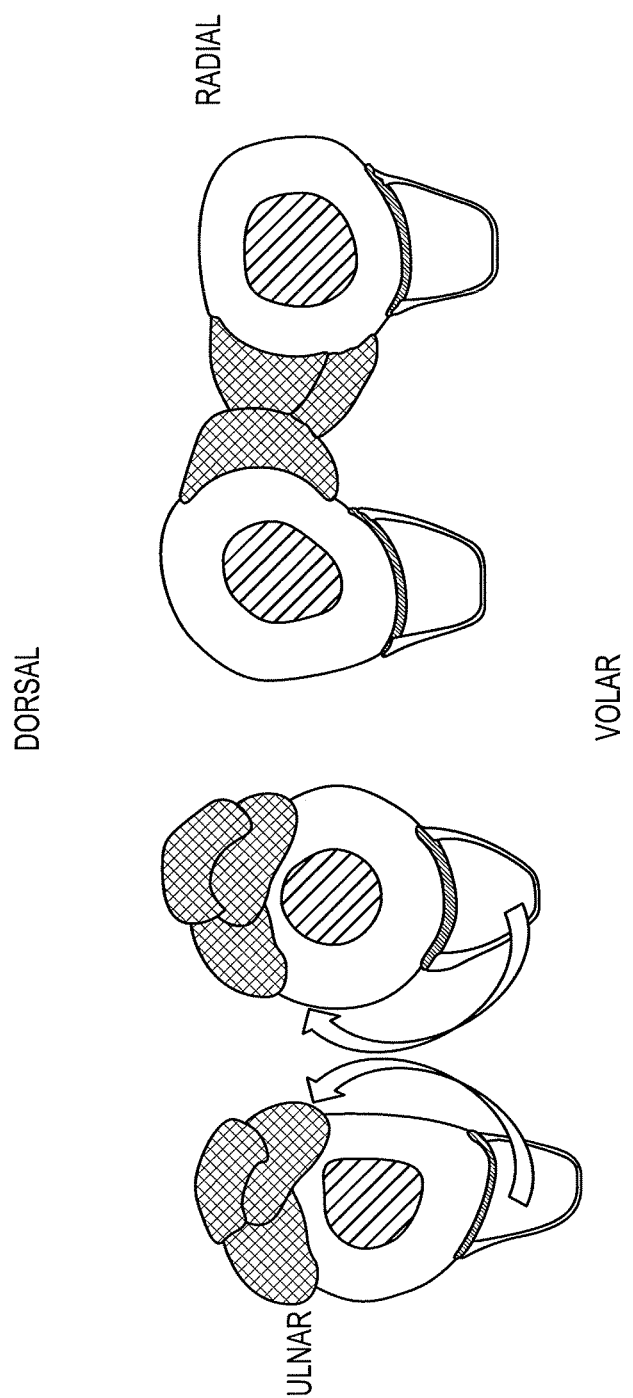
Figure 8:
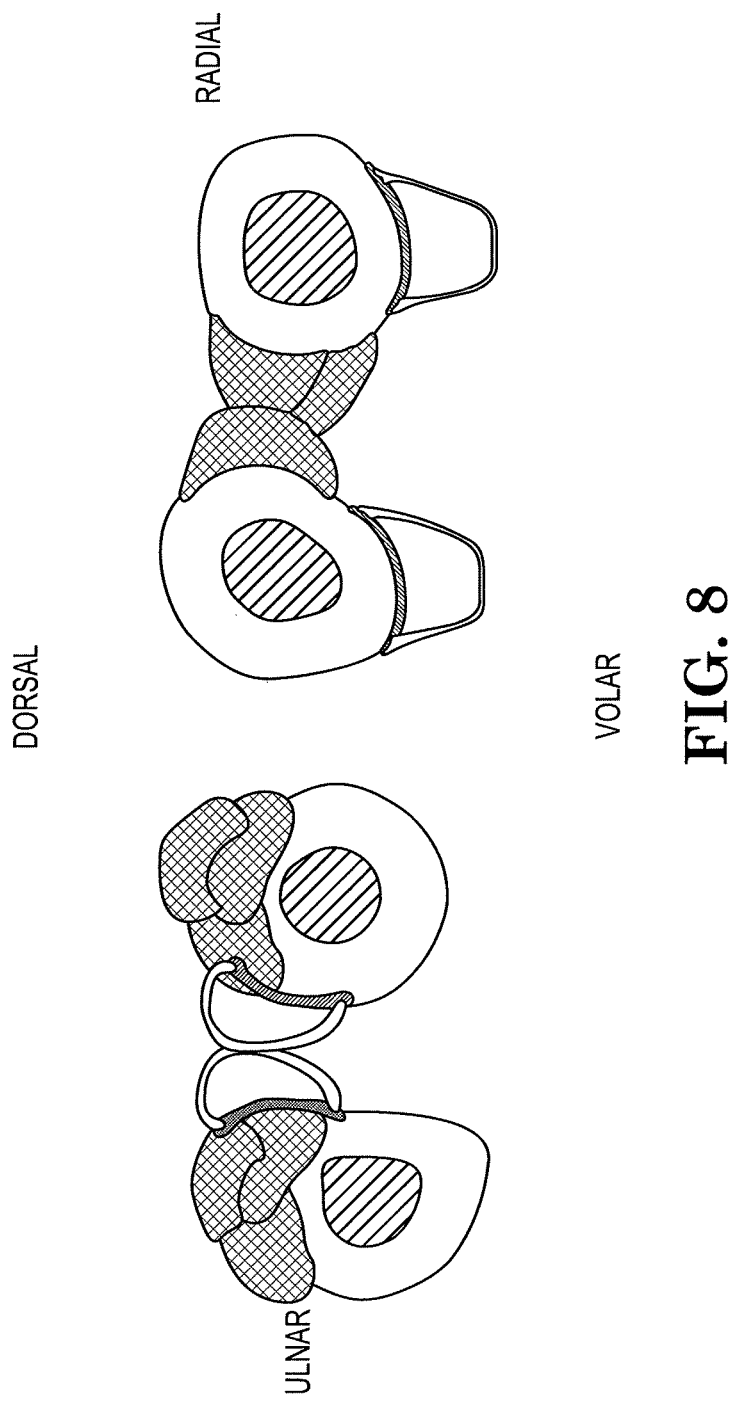
Figure 9:
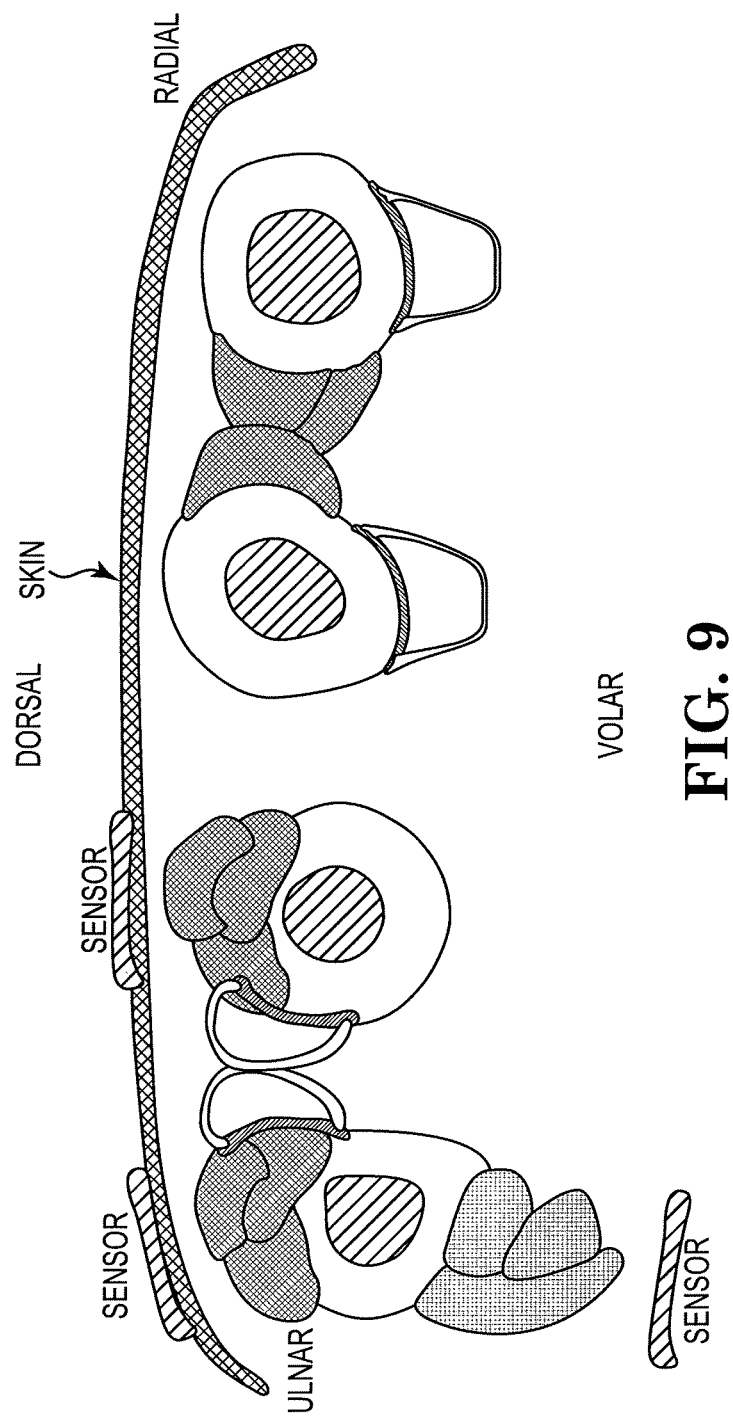
Figure 10:
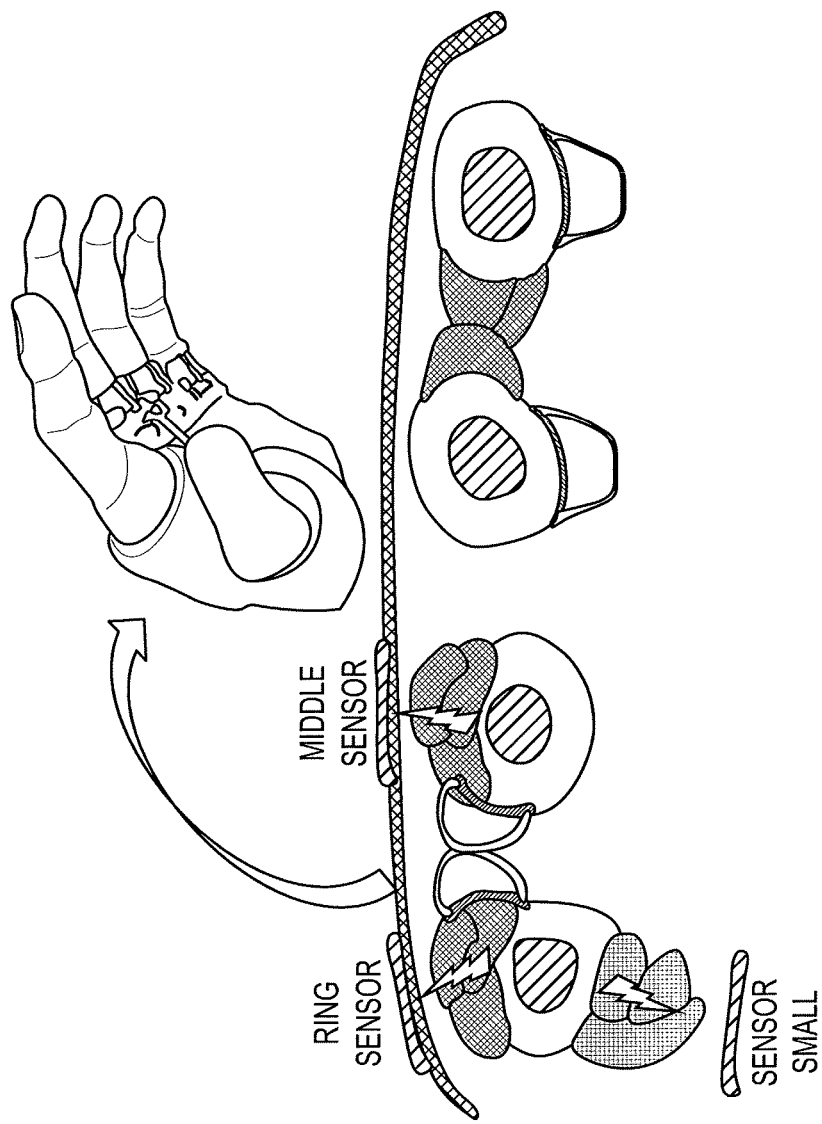
Figure 11:
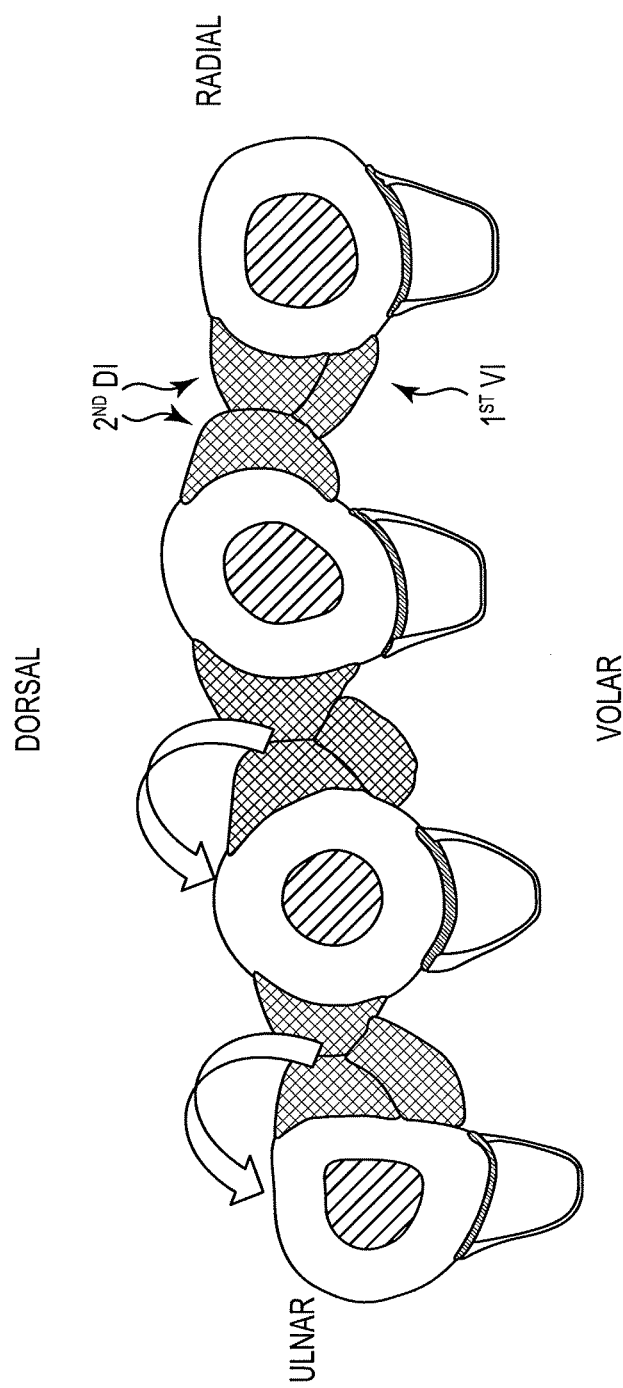
Figure 12:
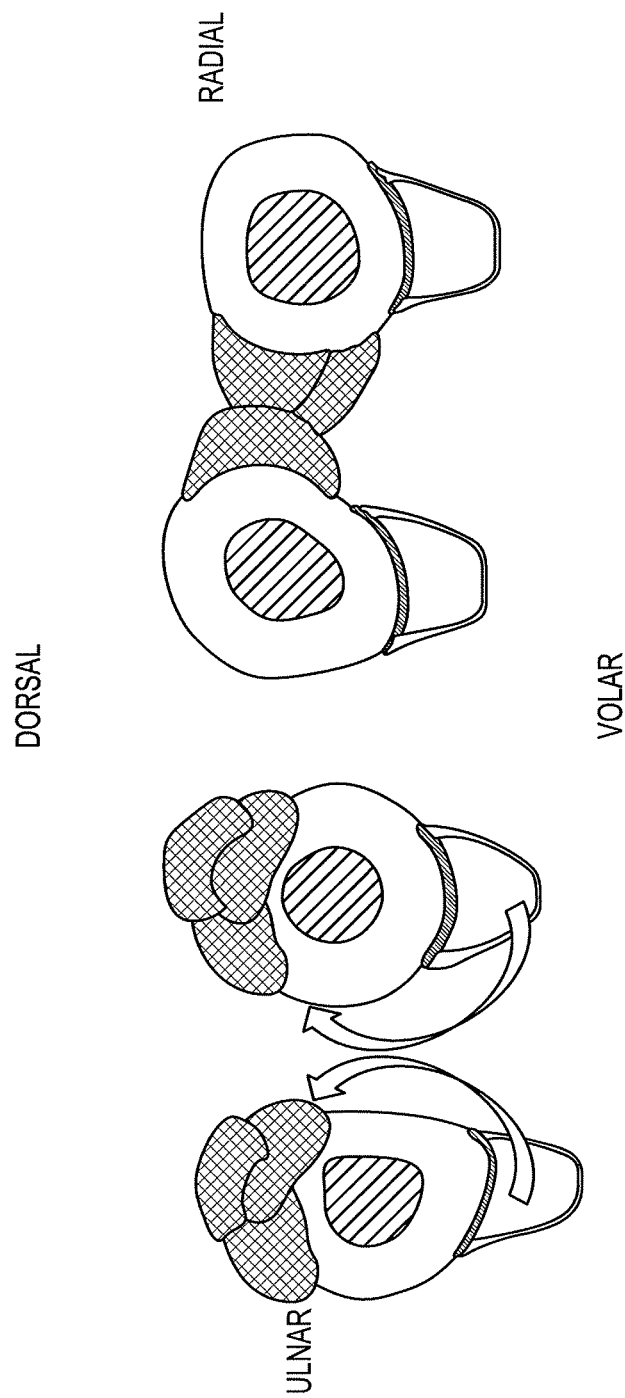
Figure 13:
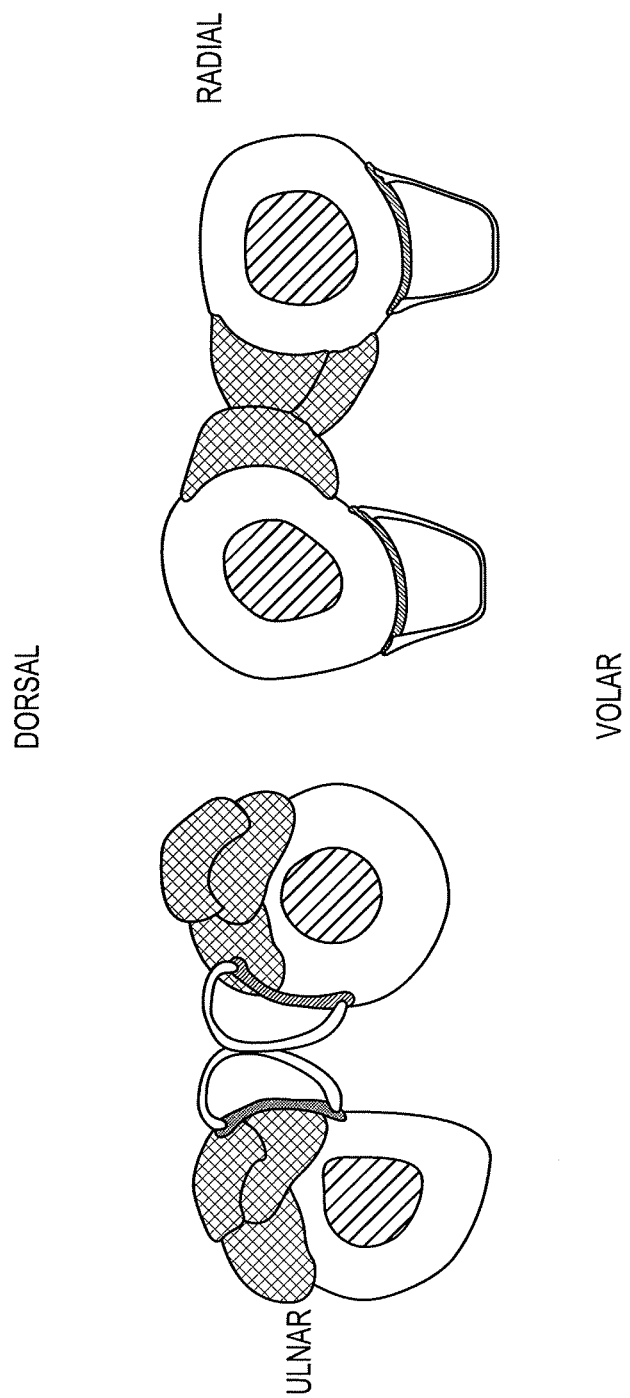
Figure 14:
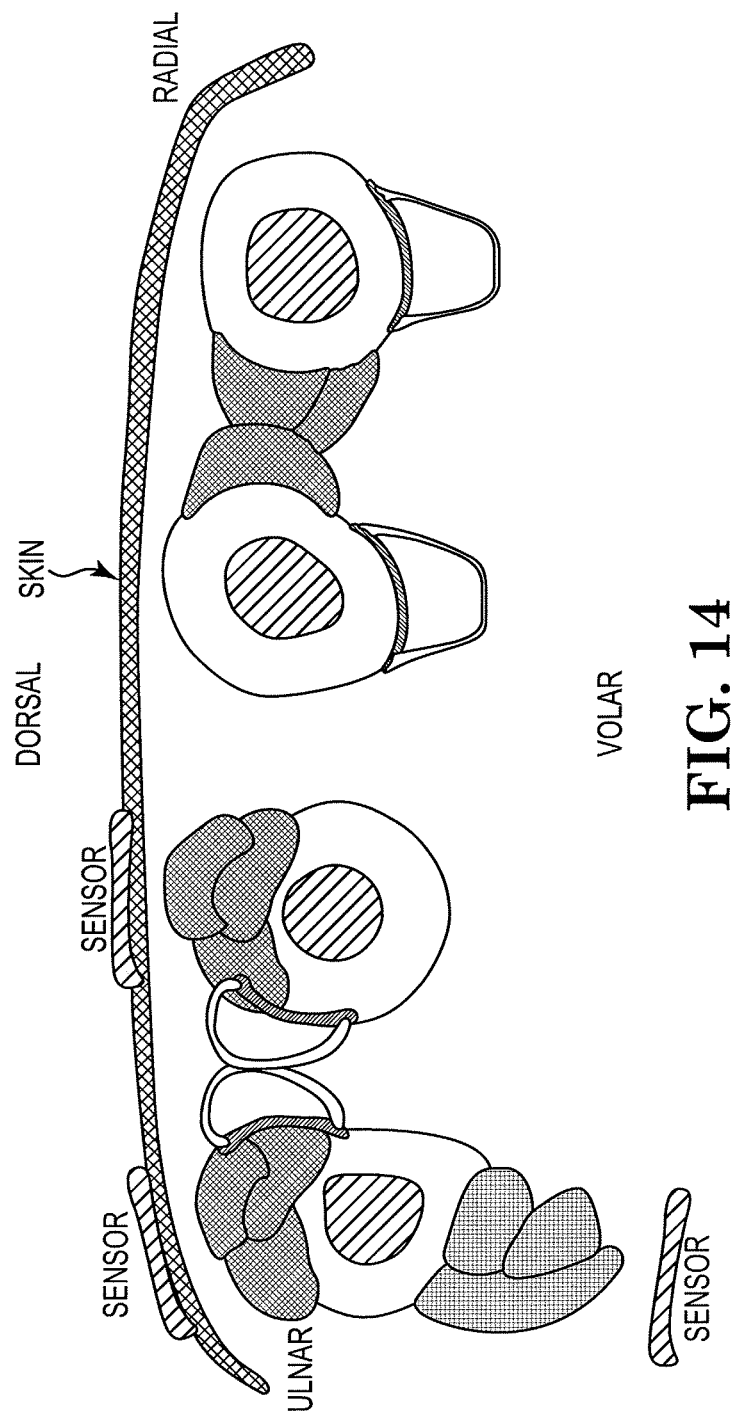
Figure 15:
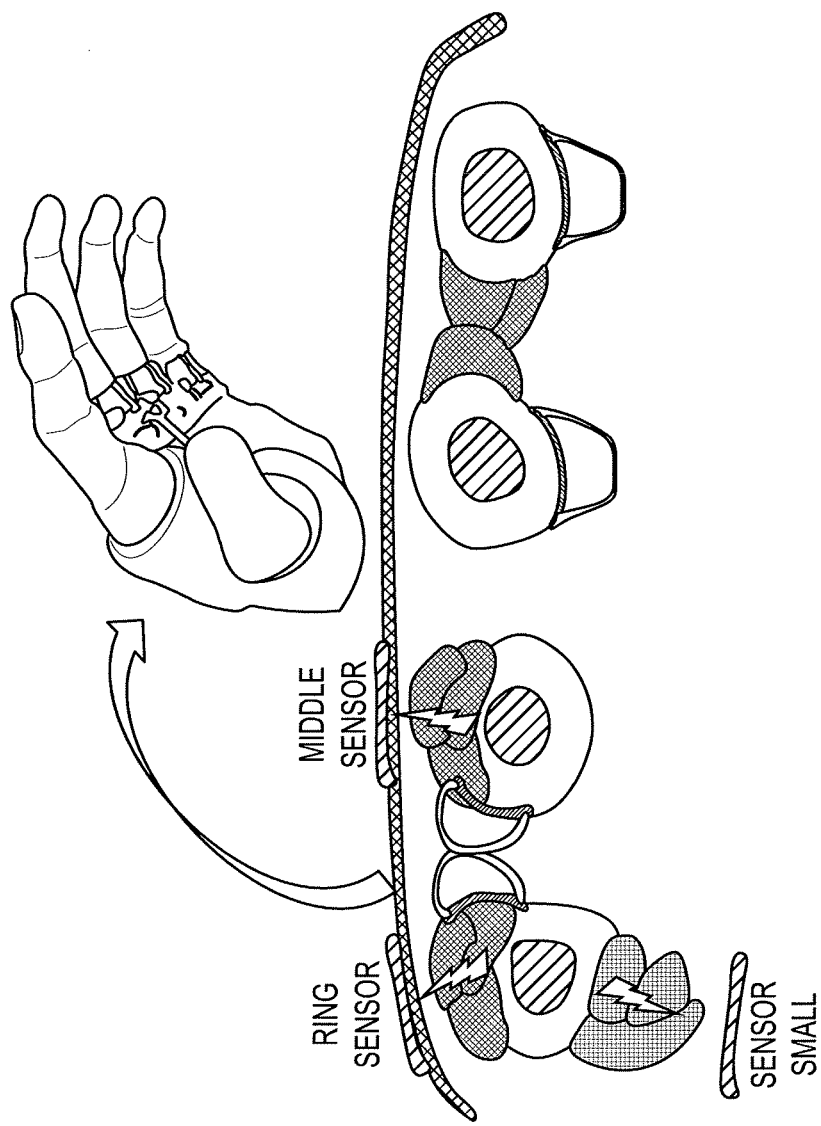

Also in amputations between the elbow and wrist, traditional myoelectric prostheses have used the signals from the flexor pronator mass for digital flexion and used signals from the extensor-supinator mass for digital extension. Because of the cross-talk and depth of the other forearm muscles, functions such as wrist flexion, extension, ulnar deviation, radial deviation, pronation, supination, individual digital control, independent thumb control, and thumb opposition have not been possible. With muscle transfers as described in FIGS. 3&4, multiple new signals are available to allow simultaneous, intuitive control of these functions.

For below elbow amputees, rotational control of the myoelectric hand is limited by the prosthesis to native forearm interface. Myoelectric prosthetics with wrist rotators have been developed, but intuitive control of these is not yet possible. Transfer of the pronator teres or pronator quadratus (PQ) muscles along with their neurovascular pedicle to a superficial location would allow pronation control of a myoelectric wrist rotator. Alternatively, the anterior interosseous nerve terminal branch to PQ could be transferred into a forearm muscle to achieve an intuitive signal for independent myoelectric pronation. The nerve to supinator could be transferred to a more superficial forearm muscle to create a myoelectric signal for independent supination control.

For amputations at or slightly above the elbow, these same muscles can be transferred above the elbow while maintaining their blood and nerve supplies thus again offering many additional signals for control of the prosthesis.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

We claim:

1. A method comprising:

Transferring intrinsic hand muscles of an individual together with a respective nerve and blood supply prior to or during an amputation of an upper extremity to a location proximal to the amputation to a wrist, a forearm, or a dorsum of a hand;

Maintaining the functionality of the transferred intrinsic hand muscles;

Detecting a signal of the transferred intrinsic hand muscles using at least one surface electrode; and Post upper extremity amputation, controlling independent flexion and extension of digits of a myoelectric prosthetic using the at least one surface electrode.

2. The method of claim 1 wherein transferring the intrinsic hand muscles of an individual together with a respective nerve and blood supply includes transferring thenar and hypothenar muscles and neurovascular pedicles.

3. The method of claim 1 wherein transferring the intrinsic hand muscles of an individual together with a respective nerve and blood supply includes transferring the volar plate and flexor sheath dorsally to serve as an interpositional autograft material between the transferred muscles.

* * * * *